(12) United States Patent
Ravuna et al.

(10) Patent No.: US 11,969,255 B2
(45) Date of Patent: Apr. 30, 2024

(54) DETECTION OF FRACTIONATED SIGNALS IN STABLE ARRHYTHMIAS

(71) Applicant: BIOSENSE WEBSTER (ISRAEL) LTD., Yokneam (IL)

(72) Inventors: Eliyahu Ravuna, Kiryat Ata (IL); Nir Yanovich, Haifa (IL); Natalia Etin Zait, Netanya (IL); Leonid Zaides, Atlit (IL); Meytel Segev, Haifa (IL); Elad Nakar, Timrat (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 221 days.

(21) Appl. No.: 17/548,558

(22) Filed: Dec. 12, 2021

(65) Prior Publication Data
US 2023/0181086 A1    Jun. 15, 2023

(51) Int. Cl.
| | |
|---|---|
| A61B 5/367 | (2021.01) |
| A61B 5/00 | (2006.01) |
| A61B 5/283 | (2021.01) |
| A61B 5/343 | (2021.01) |
| A61B 5/352 | (2021.01) |
| A61B 5/364 | (2021.01) |

(52) U.S. Cl.
CPC ............ *A61B 5/367* (2021.01); *A61B 5/283* (2021.01); *A61B 5/343* (2021.01); *A61B 5/352* (2021.01); *A61B 5/364* (2021.01); *A61B 5/7475* (2013.01)

(58) Field of Classification Search
None
See application file for complete search history.

(56) References Cited

U.S. PATENT DOCUMENTS

| 8,359,092 | B2 | 1/2013 | Hayam | |
|---|---|---|---|---|
| 9,456,759 | B2 | 10/2016 | Lian | |
| 2013/0006317 | A1* | 1/2013 | Keel | ............ A61N 1/36842 607/27 |

FOREIGN PATENT DOCUMENTS

EP    3326517 A1 *   5/2018   .......... A61B 5/0402

OTHER PUBLICATIONS

International Search Report for corresponding PCT Appln. No. PCT/IB2022/061185 dated Dec. 12, 2021.
(Continued)

*Primary Examiner* — Kennedy Schaetzle (57) ABSTRACT

In an example, a method includes receiving a cardiac signal that is sensed by an electrode at a tissue location inside the heart. Fractionations are identified in the cardiac signal. The fractionations identified at the tissue location are compared between first and second cardiac cycles of the cardiac signal. Based on the comparing, a likelihood is estimated, that the tissue location is causing a stable arrhythmia. Based on the estimated likelihood, the tissue location is indicated to a user as likely to be causing the stable arrhythmia.

32 Claims, 5 Drawing Sheets

(56) References Cited

OTHER PUBLICATIONS

Baumert Mathias et al:"Quantitative-Electrogram-Based Methods for Guiding Catheter Ablation in Atrial Fibrillation",Proceedings of the IEEE, IEEE. New York, US, vol. 104, No. 2,Feb. 1, 2016 (Feb. 1, 2016), pp. 416-431, XP011595871.

Frontera A et al., in "Electrogram signature of specific activation patterns: Analysis of atrial tachycardias at high-density endocardial mapping," Heart Rhythm. Jan. 2018;15(1):28-37.

"A new approach for automated location of active segments in intracardiac electrograms," World Congress on Medical Physics and Biomedical Engineering, Sep. 7-12, 2009, Munich, Germany, Nguyen M.P. et al.

\* cited by examiner

DETECTION OF FRACTIONATED SIGNALS IN STABLE ARRHYTHMIAS

FIELD OF THE DISCLOSURE

This disclosure relates generally to analysis of electrophysiological (EP) signals, and specifically to a method for detecting fractionated electrograms in stable arrhythmias.

BACKGROUND OF THE DISCLOSURE

Isolating complex fractionated atrial electrograms (CFAEs) to characterize an arrythmia was previously suggested in the literature. For example, in the conference paper "A new approach for automated location of active segments in intracardiac electrograms," World Congress on Medical Physics and Biomedical Engineering, Sep. 7-12, 2009, Munich, Germany, Nguyen M. P. et al. describe a method to locate signal complexes corresponding to electrophysiological activity. The disclosed method identifies CFAE by applying a Non-Linear Energy Operator (NLEO) followed by Gaussian smoothing to time-discrete atrial EGM signals. The method can this way identify areas in atrium tissue with complex fractionated atrial electrograms (CFAEs) that are, among others, responsible for the maintenance of atrial fibrillation (AFib). Those areas are ideal target sites for ablation to eliminate AFib and restore normal rhythm. The method introduces automated identification of CFAEs with signal processing algorithms to assist to develop an objective strategy for AFib ablation. The idea behind this algorithm is based on the idea of Pan-Tompkins' QRS-detection algorithm. However in this approach, the extracted signal feature is the signal energy and therefore the algorithm takes into account not only information of the frequency but also of the amplitude. With adaptive thresholding the algorithm is capable to manage changes in the signal dynamics. The results were validated by experts and the algorithm shows a robust performance.

As another example, Frontera A et al., in "Electrogram signature of specific activation patterns: Analysis of atrial tachycardias at high-density endocardial mapping," Heart Rhythm. 2018 January; 15(1):28-37, describe results from twenty-five consecutive patients that underwent high-density atrial mapping during atrial tachycardias. Bipolar EGMs were recorded with a 64-electrode basket catheter. The following atrial phenomena were identified: slow conduction (SC) areas, lines of block (LB), wavefront collisions (WFC), pivot sites (PS), and gaps. EGMs collected at these predefined areas were analyzed in terms of amplitude, duration, and morphology. It was found that specific EGM characteristics in atrial tachycardia can be reproducibly linked to electrophysiological mechanisms. High-voltage and short-duration EGMs are associated with collision sites and PS that are unlikely to form critical sites for ablation; long-duration, low-voltage EGMs are associated with SC. However, not all SC regions will lie within the critical circuit and identification by only EGM characteristics cannot guide ablation.

BRIEF DESCRIPTION OF THE DRAWINGS

The present disclosure will be more fully understood from the following detailed description of the examples thereof, taken together with the drawings, in which.

DETAILED DESCRIPTION OF EXAMPLES

Overview

A stable arrhythmia, such as an atrial flutter or a stable ventricular tachycardia (VT), is often defined as a sustained arrhythmia not associated with significant hemodynamic compromise. However, a stable arrythmia can readily deteriorate into life-threatening conditions, and therefore, once diagnosed, it requires prompt treatment, including an option to ablate arrhythmogenic tissue locations that cause the stable arrhythmia.

In order to characterize a stable arrhythmia of a patient, a catheter-based electrophysiological (EP) mapping system may be used to generate an EP map of least part of the heart of the patient, such as an EP map of a cardiac chamber. In a typical catheter-based EP mapping procedure, a distal end of a catheter, which comprises one or more sensing electrodes, is inserted into the cardiac chamber to sense EP signals, such as bipolar electrograms (EGM). As a physician operating the system moves the distal end inside the cardiac chamber, the EP-mapping system acquires EP signals at various locations on the inner surface of the cardiac chamber, as well as the respective positions of the distal end. Based on these acquired signals, a processor of the mapping system generates the required EP map comprising local EP tissue characteristics (e.g., local cycle time between activations) overlaid on an anatomical map of the cardiac chamber.

When mapping a stable arrhythmia (e.g., stable tachycardia), a physician looks for particular areas on a surface of cardiac tissue having aberrant EP characteristics, i.e., one or more tissue isthmuses, to ablate. Typically, isthmuses are EP-conducting areas between adjacent scars or between natural structural barriers and scars, since such areas facilitate stable arrhythmias. Isthmuses are characterized by EP signals having fractionated activations.

Present systems using current algorithms for identifying and characterizing a stable arrhythmia do not provide good pointers to areas for a physician to ablate, so the physician typically has to perform time-consuming checking of candidate tissue locations before ablation.

Electrograms that are fractionated (e.g., comprising irregular patterns such as bursts of highly rapid deflections of the EGM) can be classified into two major types. Some fractionated electrograms exhibit no characteristic cycle time. Other fractionated electrograms show a nearly characteristic cycle time between episodes of signal fractionation.

Examples of the present disclosure that are described herein provide improved methods and systems for mapping cardiac tissue locations that exhibit a nearly periodic cycle time, which is a characteristic of stable arrhythmias, such as left atypical atrial flutter. The disclosed technique identify electrograms exhibiting repeatable fractionated signals, and use these electrograms to map cardiac tissue locations likely to be causing a stable arrhythmia.

With the disclosed techniques, the physician is presented with an EP map overlayed with tissue locations likely to cause a stable arrhythmia. The likelihood measure may be configurable by the physician. Given the disclosed presentation, the physician can readily and interactively assess the map in order to decide which cardiac tissue locations exhibit stable arrhythmia and whether to ablate tissue there.

Some examples of the present disclosure that are described herein therefore provide methods and systems to automatically identify and analyze cardiac tissue areas causing a stable arrhythmia by identifying and analyzing electrograms exhibiting recurring fractionations.

In some examples a processor may analyze intracardiac electrogram (EGM) and/or body surface electrocardiogram (ECG) signals to calculate the arrhythmia cycle length, and then identify fractionated activations that are repeatable from beat to beat in the EGM. Although these activations are not exactly repeatable, they are sufficiently repeatable for the disclosed algorithm to identify such repeatable fractionations by comparing a present heartbeat (i.e., cardiac cycle) with some previous heartbeat (that can occur a given number of heartbeats before, during a same mapping session).

In addition to identifying repeatable fractionations, the algorithm characterizes the fractionations, for example by finding their duration ΔT (in time) and also their temporal location T in the cardiac cycle. Both of these quantities are relevant in locating an isthmus. The longer the fractionation, the higher the chance of the fractionation being indicative of arrhythmogenic tissue. In terms of location, if the timing of fractionation occurrence, T, occurs in a mid-diastolic region of the cardiac cycle, it is also likely to be highly indicative of arrhythmogenic tissue.

In some examples, the disclosed algorithm relies on applying a Non-Linear Energy Operator (NLEO) to an input EP signal. The NLEO amplifies the fractionations, and applying a Gaussian filter to the NLEO result gives a smoothing envelope effect to the fractionated signals.

The disclosed algorithm includes the following main steps:
(i) Receiving a cardiac signal that is sensed by an electrode at a tissue location inside the heart;
(ii) Identifying fractionations in the cardiac signal (e.g., over a heartbeat of the signal);
(iii) Comparing the fractionations with fractionations found over a previous cardiac cycle (e.g., between first and second cardiac cycles);
(iv) Based on the comparison, estimating a likelihood that the tissue location is causing a stable arrhythmia (e.g., by estimating a likelihood of the fractionation in the signal being indicative of stable arrhythmia); and
(v) Based on the estimated likelihood, indicating the tissue location to a user (e.g., with a score) as likely to cause stable arrhythmia. A minimal score means the location is unlikely to cause stable arrhythmia and a maximal score means the location very likely will cause stable arrhythmia.

Further algorithm steps may include:
Calculation of a baseline noise of the EP signal to adjust a threshold of the NLEO calculation dynamically according to the baseline noise.
Capping the EP signal before the application of the NLEO calculation to improve results of the NLEO calculation.
Finding fractionations by using the EP signal amplitude, alongside with the NLEO.
Representing fractionation windows as triangles between 0 and 1, to facilitate identification of a shift in timing of the fractionation.
Representing fractionation windows as rectangles between −1 and 1, to obtain a quick measure of the similarity between the beats (speeding up CPU calculations).
Requiring a minimum similarity between the beats.
Requiring the peak-to-peak of the current and previous beats to be similar as a sanity test.
Measuring a "silence ratio" as time duration without fractionations divided by total cycle time. This ratio may be used as an input to a machine learning classifier, such as logistic regression, or it may be used as part of a sanity test to differentiate repeatable fractionations from irrelevant irregular fractionations. For example, a very long fractionation with almost no silence between the fractionations is an indication of noise.
Using the following as features in a classifier, for example logistic regression classifier:
Duration of candidate fractionation.
Number of candidate fractionations per duration.
Number of zero crossings per duration.
Log of number of wavefront candidates (as counted by annotations). The calculation of wavefront annotation candidates are taught in U.S. Pat. No. 9,380,953, and in U.S. Pat. No. 11,071,489.
Silence ratio, which may be capped by a maximum limit.
"Aspect ratio" of the candidate fractionation, calculated as peak-to-peak signals divided by the duration. A higher aspect ratio means it is more likely a true fractionation (and not noise).
A user interface to dynamically select the threshold for the classifier, and to highlight the fractionation areas on the map according the status of the slider in real time while the user moves the slider.
Displaying fractionated areas in real time (while the user moves the threshold scoring slider) so the user can intuitively select the right balance between sensitivity and specificity.

For each given EP signal, the algorithm returns a fractionation score. The user sets a threshold for the fractionation score to balance between sensitivity and specificity. A typical fractionation score can be a number between 0 and 10 that predicts the likelihood of a fractionation component in the signal inside the time frame. 0 means the likelihood of a fractionation occurring is low, 10 means the likelihood of a fractionation occurring are high. The score can guide the physician performing the EP mapping where to look for the isthmus tissue.

The rationale of using a fractionation score between 0 and 10 is to prevent any confusion with statistical probability. One could as-well use a fractionation score between 0 and 100. But users could misunderstand 100 as a 100% probability of a fractionation. Therefore, we think a fractionation score between 0 and 10 is a better choice. A fractionation score of 10 means that the probability of a fractionation is quite high, but still does not mean 100% probability.

Cardiac conditions with stable arrhythmias where repeatable fractionations are relevant include, but are not limited to, atypical flutter, focal atrial tachycardia (AT), and ischemic VT. Therefore, by applying the disclosed methods, tissue locations causing numerous stable arrhythmias may be more accurately pinpointed, leading to safer and more effective treatment of stable arrhythmias with ablation.

System Description

Figure 1:
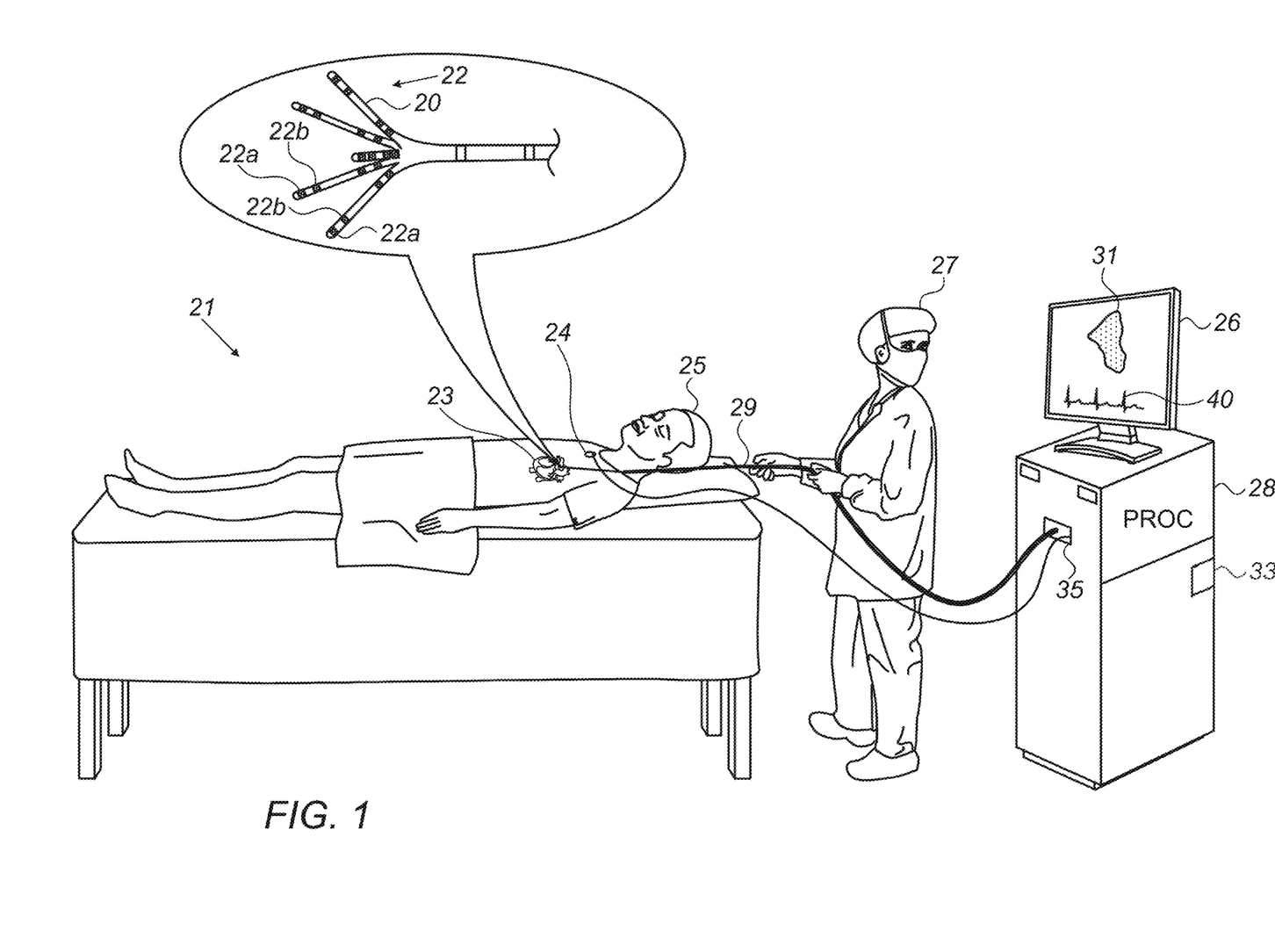
FIG. 1 is a schematic, pictorial illustration of a catheter-based electrophysiological (EP) mapping system, according to an example of the present disclosure.

FIG. 1 is a schematic, pictorial illustration of a catheter-based electrophysiological (EP) mapping system 21, according to an example of the present disclosure. FIG. 1 depicts a physician 27 using an electro-anatomical mapping catheter 29 to perform an electro-anatomical mapping of a heart 23 of a patient 25. Mapping catheter 29 comprises, at its distal end, one or more arms 20, each of which is coupled to a bipolar electrode 22 comprising adjacent electrodes 22a and 22b.

During the mapping procedure, the locations of electrodes 22 are tracked while they are inside heart 23 of the patient. For that purpose, electrical signals are passed between electrodes 22 and external electrodes 24. For example, three external electrodes 24 may be coupled to the patient's chest, and another three external electrodes may be coupled to the patient's back. (For ease of illustration, only one external electrode is shown in FIG. 1.)

Based on the signals, and given the known positions of electrodes 24 on the patient's body, processor 28 calculates an estimated location of each electrode 22 within the patient's heart. Respective electrophysiological data, such as bipolar electrogram traces, are additionally acquired from tissue of heart 23 by using electrodes 22. The processor may thus associate any given signal received from electrodes 22, such as a bipolar EP signal, with the location at which the signal was acquired. A processor 28 receives the resulting signals via an electrical interface 35, and uses information contained in these signals to construct an electrophysiological map 31 and EGM or ECG traces 40, and to present these on a display 26. The EGM or ECG traces 40 are also stored in a memory 33 for use with the disclosed algorithm. One tracking system and method capable of producing map 31 is the Advanced Current Location (ACL) system, implemented in various medical applications, for example, in the CARTO™ system, produced by Biosense-Webster Inc., which is described in detail in U.S. Pat. No. 8,456,182 whose disclosure is incorporated herein by reference.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm as disclosed herein, including in FIG. 2, that enables processor 28 to perform the disclosed steps, as further described below.

The example illustration shown in FIG. 1 is chosen purely for the sake of conceptual clarity. Other types of electrophysiological sensing catheter geometries, such as the Lasso® Catheter (produced by Biosense-Webster Inc., Irvine, Calif.) may be employed. Additionally, contact sensors may be fitted at the distal end of mapping catheter 29 to transmit data indicative of the physical quality of electrode contact with tissue. In an example, measurements of one or more electrodes 22 may be discarded if their physical contact quality is indicated as poor, and the measurements of other electrodes may be regarded as valid if their contact quality is indicated as sufficient.

Detection of Fractionated Signals in Stable Arrhythmias

Figure 2:
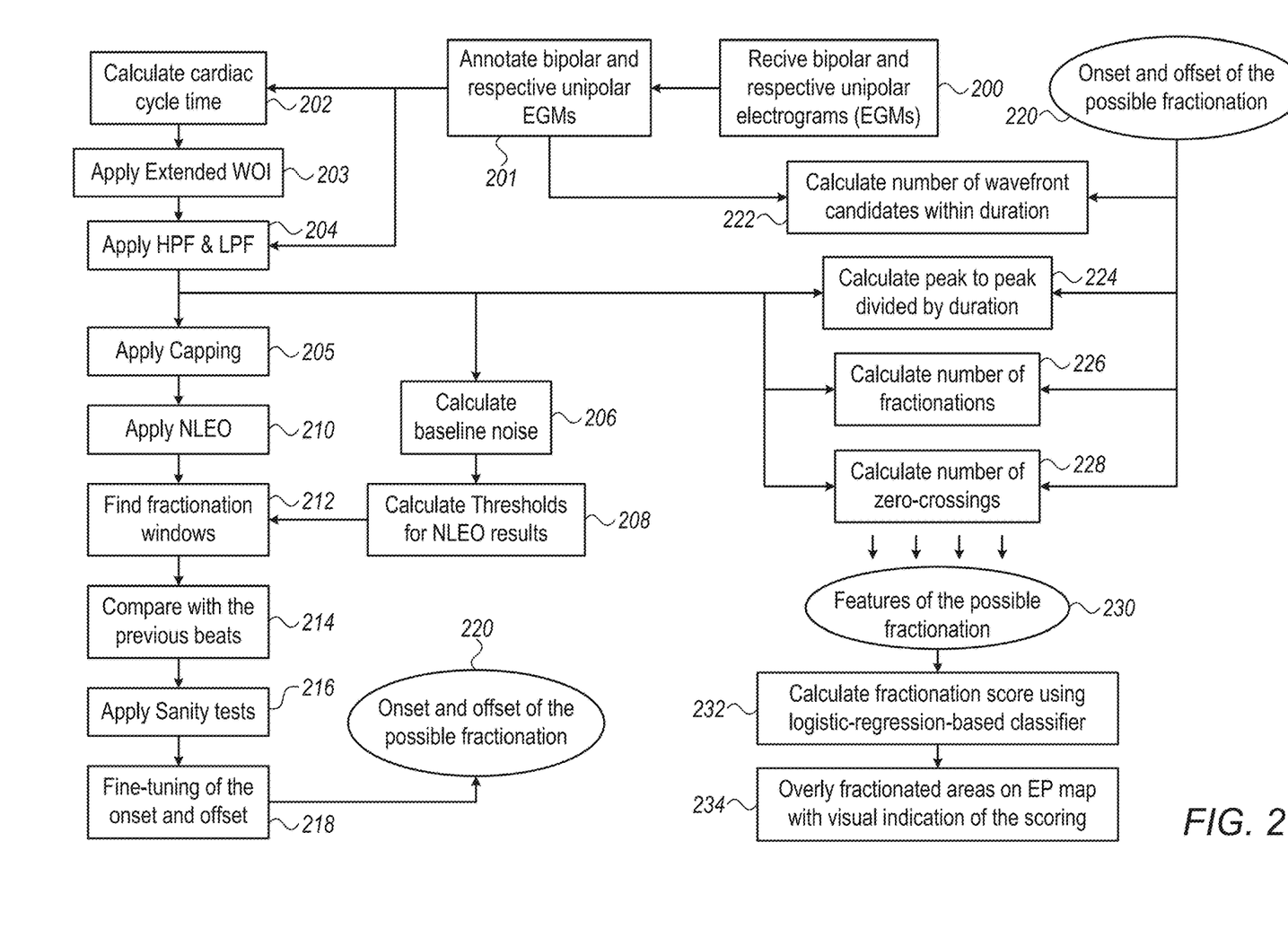
FIG. 2 is a flow chart that schematically illustrates a method and algorithm for the detection of fractionated signals in stable arrhythmias, according to an example of the present disclosure.

FIG. 2 is a flow chart that schematically illustrates a method and algorithm for the detection of fractionated signals in stable arrhythmias, according to an example of the present disclosure. The algorithm, according to the presented example, carries out a process that begins with a processor, such as processor 28, receiving (i) a bipolar signal (e.g., waveform) from catheter 29, and (ii) a respective unipolar signal, at a cardiac signal receiving step 200. In the shown example, processor 28 receives a unipolar component of the bipolar EGM. Both signals are received and sampled in 1 kHz, in millivolts, after power line interfere rejection.

Next, at an annotating step 201, processor 28 annotates the activations of the bipolar and the respective aforementioned unipolar EGMs.

Using the annotations, processor 28 calculates cardiac cycle times (also called cycle lengths (CL)), as a time difference between current and previous reference annotations, in milliseconds, at a cycle time estimation step 202.

The processor then applies an extended window of interest (WOI) to the bipolar signal, which is a time-duration window larger than the calculated cycle length (typically 120% of the estimated CL), at application of WOI step 203. Steps 201-203 enable isolation of a bipolar waveform for analysis, such as a bipolar waveform 301 seen in FIG. 3 below. In particular, using the extended WOI ensures capturing, in full, all fractionations of the signal that start within the cardiac cycle to be analyzed. The rationale for using the extended WOI is that mid-diastolic fractionations, which are clinically relevant, may be present in the middle of two consecutive WOIs. Namely, the fractionation starts before the end of one WOI and continues after the start of the next consecutive WOI. The extended WOI helps detect these fractionations by allowing a fractionation to end after the nominal WOI.

Next, at a signal filtration step 204, processor 28 applies high-pass and low-pass filters (HPF and LPF) to the bipolar signal to further clean the signal.

Next, at a signal capping step 205, processor 28 applies capping to the bipolar signal. In this step, the magnitude of the bipolar EGM is capped between lower and upper cap values. The input of the capping process is the signal after HPF and LPF, the output being the capped EGM. In an example, the upper cap value is calculated as the N'th (e.g., N=10) largest sample of the signal in the extended WOI, while the lower cap value is calculated as an M'th lowest (e.g., M=10) sample of the signal in the extended WOI. The rationale for using N=M=10th largest and lowest samples is that EGM peaks are usually 10-20 ms wide. Therefore, if there is an activation (e.g., far field activation effect) in the signal, excluding 20 samples (10 largest and 10 lowest samples) roughly excludes the large irrelevant activations which would otherwise distort the subsequent NLEO analysis.

At a baseline calculation step 206, processor 28 defines the baseline noise in the WOI as the minimum value of a "sliding maximum window" of the absolute value of the signal. The width of the sliding maximum window is some constant ratio (e.g., 20%) of the cardiac cycle length, but never narrower than some given duration (e.g., 35 ms). The lower limit of 35 ms does not have any effect if the cycle length is larger than 175 ms, which means 342 atrial beats per minute, because, when the cycle length is larger than 175 ms, the window size is larger than 35 ms. An example of this scheme in shown FIG. 3 to find a baseline noise segment 305 with the lowest maximum absolute value.

Typically, the same process is repeated for the two previous cardiac cycles, and the largest baseline noise among the last three cardiac cycles is considered as the baseline noise of the signal.

The rationale for 20% segment length is that, even if assuming that there is an interference of the ventricular far field in one of the last three beats, and even if there is a very long fractionation, there should still be a continuous silence during at least 20% of the cardiac cycle time somewhere in the WOI (based on at least a minimal predefined portion of the cardiac cycle not containing any fractionation). Therefore, the maximum absolute value of the signal in the most silent 20% segment is considered as the baseline noise. However, there can be fractionations that are larger than 80% of the cycle length, and in these cases, the baseline noise may be overestimated. The baseline noise is used in the calculation of the number of fractionations and the NLEO threshold constant only. Although an overestimated baseline noise reduces the chances that a fractionation will be detected, since the disclosed logistic regression classifier uses multiple features the fractionation can still be detected even if the baseline noise is overestimated.

Next, at NLEO thresholds calculation step 208, processor 28 uses the baseline noise and EGM-capped amplitude to calculate two threshold values that will be applied to the NLEO results to find windows where fractionations valid for further analysis occur. The first threshold value, called hereinafter K, is used with a sliding standard deviation operator applied to the result of the Gaussian filtered NLEO results. In this first thresholding step, the result of the sliding standard deviation is multiplied with a constant K to obtain the threshold. The K value is dynamically adjusted in the disclosed method to minimize false positive detection of fractionation. In the disclosed algorithm, the processor dynamically adjusts the K value according to the ratio between the baseline noise and the peak-to-peak value of the EGM signal. In this way K typically varies between 0.15 for clean signals and 0.35 for noisy signals.

The second threshold is applied on the amplitude of the Gaussian-filtered NLEO results. Although NLEO is better than mere amplitude as a predictor of fractionations, the amplitude still needs to be taken into consideration to prevent noise from being detected as a fractionation. To this end, a sample is considered to be part of a fractionation component only if its amplitude is larger than, typically, several μV, which is the resolution of the acquisition hardware, or two times larger of the baseline noise, whichever is larger.

Figure 4:
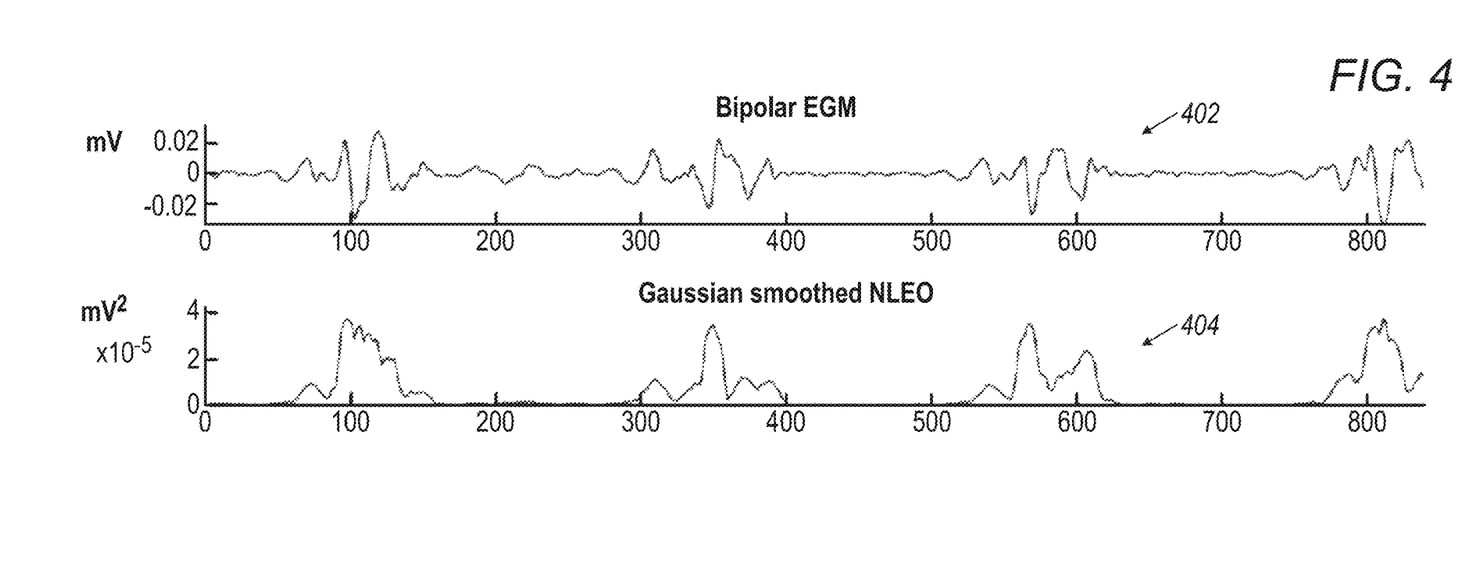
FIG. 4 shows example graphs of an electrogram acquired using the system of FIG. 1, and the signal after applying the NLEO and Gaussian filter step described in FIG. 2, according to an example of the present disclosure.

At an applying NLEO step 210, processor 28 applies the NLEO to the bipolar EGM and afterwards applies a smoothing Gaussian filter to the output of the NLEO, with an example of the resulting waveform given in FIG. 4. As seen in FIG. 4, the result (e.g., waveform 404) of step 210 amplifies the visibility of the fractionations in a bipolar EGM 402.

Figure 5:
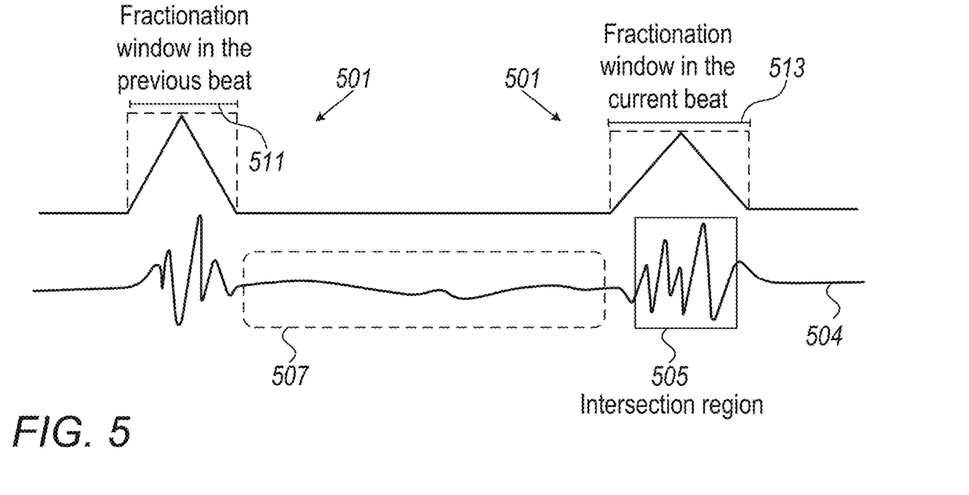
FIG. 5 is a graph that schematically shows two fractionations with respective windows found in a step described in FIG. 2, and an intersection region of the windows, according to an example of the present disclosure.

Next, at a finding fractionation windows step 212, processor 28 finds fractionation windows, such as windows 501 of FIG. 5. The fractionation windows may be rectangles in the modulation pattern, 0 in the vertical axis meaning there is no fractionation, 1 in the vertical axis meaning there is a fractionation at that time. In a next step, in order to make it easier to align the center of the fractionation window in the previous and current heartbeats, the fractionation windows are represented as isosceles triangles. During the rest of the algorithm, fractionation windows are represented as isosceles triangles. In such a case the modulation 0 in the vertical axis means there is no fractionation at that time, while any positive value in the vertical axis means there is a fractionation at that time. As seen, the maximum height in the vertical axis is the center of the fractionation window.

Fractionation windows with a gap of less than 30 ms are united. The rationale for 30 ms is the following: the absolute refractory period of healthy cardiac cells lasts about 180 ms. One of the two required conditions to sustain a reentry in the cardiac tissue is a short refractory period (the other has slow conduction). Therefore, in the isthmus, the absolute refractory period is expected to be shorter. However, 30 ms is six times lower than this number. Hence, if the gap between two fractionation windows is less than 30 ms, it is reasonable to assume that this cannot be a new activation, and that it is either noise or a continuation of the same activation. In both cases, the activations are united. If the second fractionation window is noise, the comparison with the previous beats, done in a subsequent step, should, in any event, eliminate this section of the fractionation.

Figure 8:
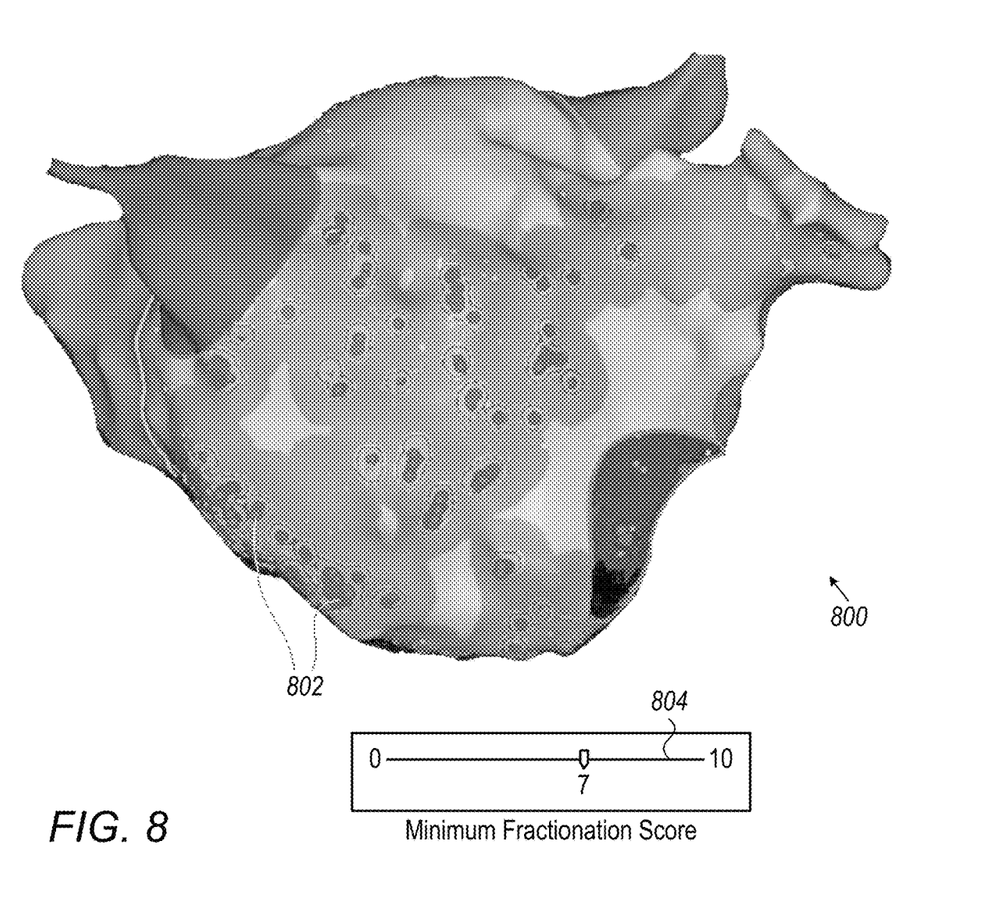
FIG. 8 is a schematic, pictorial volume rendering of an EP map of a ventricle indicating tissue locations and magnitude of fractionations that may cause a stable arrhythmia, according to an example of the present disclosure.

Consistency between heart beats is one of the most significant disclosed predictors of fractionation that lead to successful mapping of a stable arrhythmia (such a map illustrated in FIG. 8). The rationale is that, in stable arrythmias, in a case with 1:1 atrioventricular conduction, all heart beats should exhibit a similar morphology. In a case with 1:N atrioventricular conduction, all beats without any "overlap of ventricular activity" should also be similar. Therefore, the current beat should be similar either to the previous beat or to the one before the previous.

Some heart beats may be shadowed by the ventricular activation far-field signal, therefore the most similar beat may be the previous one or the one before the previous beat.

The timing of the fractionation can also exhibit some shift among the beats. To solve the problem of the shift, processor 28 compares the fractionations in windows in the current extended WOI with the two previous extended WOIs, at a fractionation comparison step 214. In other words, the processor compares the fractionations, identified at the tissue location, between first and second cardiac cycles of the cardiac signal. In an example, processor 28 changes a shift between from −20 ms to 20 ms with steps of 2 ms while correlating the fractionations. The shift that gives the highest correlation (e.g., dot product) is considered the best shift. However, comparing fractionations between different beats is challenging because, although the timing of the fractionations in the cycle length is sufficiently stable, the exact morphology of the fractionations tends to vary between the beats. To solve this problem, the disclosed technique detects the start and end times of the fractionation windows, converts the windows into triangles, as shown in FIG. 5, and performs the correlation (e.g., dot product) on the signals converted to triangles, instead of correlating the signals themselves. The triangle form ensures that the centers of the fractionation complexes are aligned as much as possible.

Once the shift is determined for the two previous beats, the fractionation windows as rectangles are transformed to the scale between −1 and +1 and the dot product is calculated between the current beat and the previous two beats. The result of this dot product is divided by the number of samples in the extended WOI to get a measure of the similarity between the two beats.

Transforming the vertical axis to between −1 and 1 results in the following scheme. Any matching sample contributes to the similarity positively, whereas any non-matching sample enacts a cost on the similarity:

| Previous Beat | Current Beat | Sign of Correlation | Comments |
|---|---|---|---|
| −1 | −1 | 1 | If both samples belong to a non-fractionated segment, they are positively correlated |
| 1 | 1 | 1 | If both samples belong to a possible fractionation, they are positively correlated |
| −1 | 1 | −1 | If the sample in one beat belongs to a fractionation window, they are negatively correlated. |
| 1 | −1 | −1 | |

When the dot product is divided by the number of samples in the extended WOI, the resulting measure of similarity is a real number between −1 and 1.

Among the two previous beats, the one with the highest similarity score is considered as the most similar beat.

Next, to validate step 214, processor 28 runs "sanity checks" at a sanity test application step 216.

A sanity test is performed to decide whether to stop the algorithm and return a fractionation score equal to zero without any further processing. If the sanity test fails, it is assumed there is not enough information to output any non-zero fractionation score. As a design principle, the algorithm favors specificity over sensitivity. In other words, a false negative is preferred over a false positive. Therefore, if the sanity test fails, the algorithm stops here.

The sanity test succeeds if all the following conditions are met. The constants in the following clauses are given as typical examples.

(1)—The peak-to-peak of the most similar previous beat is at least one third of the peak-to-peak of the current beat in the whole extended WOI. Otherwise, the previous beat is assumed to be mere noise.

(2)—The peak-to-peak of the current beat is at least one third of the peak-to-peak of the most similar previous beat in the whole extended WOI. Otherwise, the current beat is assumed to be mere noise.

(3)—The similarity measure calculated in the previous step is at least a given fraction (e.g., at least by 0.5).

(4)—The largest fractionation window anywhere in the previous three beats is at most a maximal portion (e.g., 80%) of the cycle length. Otherwise, it is assumed that at least some of the fractionation windows represent noise and the beat is discarded because the algorithm favors a false negative over a false positive.

(5)—The onset and offset of the potential fractionation do not differ more than a given fraction (e.g., half fractionation) of duration in the current and most similar previous beat. The sum of the differences of onset and offset is, at most, a given percentage (e.g., 75%) of the fractionation duration (after taking into consideration the shift to obtain the best similarity).

(6)—The duration of the fractionation component is at least a given time duration (e.g., at least 30 ms).

The rationale of sanity check 6 (e.g., using a time duration of 30 ms) is that the disclosed algorithm is designed to find fractionations of at least 30 ms. Although narrower fractionations are possible, it is challenging to differentiate such a fractionation from a normal activation. Therefore, in one example, the lower limit of 30 ms is a given limitation of the algorithm.

(7)—The duration of the fractionation component shall be, at most, a given percentage (e.g., 85%) of the WOI.

(8)—There shall be at least a minimal number (e.g., 4) of significant extrema.

(9)—At least a given percentage (e.g., 15%) of the WOI shall not contain any fractionation in the current beat and in the most similar previous beat.

The rationale of sanity check 9 (e.g., of 15%) is that the algorithm is designed, in one example, to find fractionations up to 85% of the WOI. Although larger fractionations are clinically possible, it is challenging to differentiate such a fractionation from mere noise. Therefore, the upper limit of 85% of the WOI is a limitation taken in that example of the algorithm.

As seen in FIG. 5, time durations 511 and 513 of windows 501 is different, with the intersection region 505 between the two equals smaller duration 511. Thus, to improve detection (e.g., by the classifier) for fractionations that passed the sanity checks (passed step 216), processor 28 next fine-tunes the onset and offset timings of the fractionations, at a fine-tuning step 218.

As there can be more than two windows considered for comparison, the intersection duration of fractionation windows of the current and the most similar previous beat is calculated. The largest intersection, starting in the beginning of the WOI and ending in the end of the extended WOI, is assumed to be the time frame of the possible fractionation.

The previous beats are calculated by subtracting the once or twice cycle length from the WOI. Since the cycle length is calculated as the difference between two reference annotations, the previous WOI is exact. The WOI before the previous one may differ slightly from the corresponding reference annotation. However, the WOI is, in any event, shifted left and right to find the best alignment of the fractionation windows.

The algorithm is designed to find fractionations until the end of the extended WOI. As of this example, the extended WOI is 20% beyond the end of the original WOI. In some cases, this may cause a fractionation to be split into two beats. This is a known limitation in one example of the algorithm.

Fine tuning the time frame of the possible fractionation (i.e., step 218) is done as follows: since the time frame is calculated based on the intersection between two beats, it may look prematurely trimmed on the current, longer duration, later beat, as illustrated in FIG. 5.

Thus, processor 28 first contracts the onset and offset of the time frame up to the leftmost and rightmost extrema with a voltage step of a size of at least baseline noise, e.g., 3 μV or 5% of the peak-to-peak of the potential fractionation component, whichever is largest.

Figure 6:
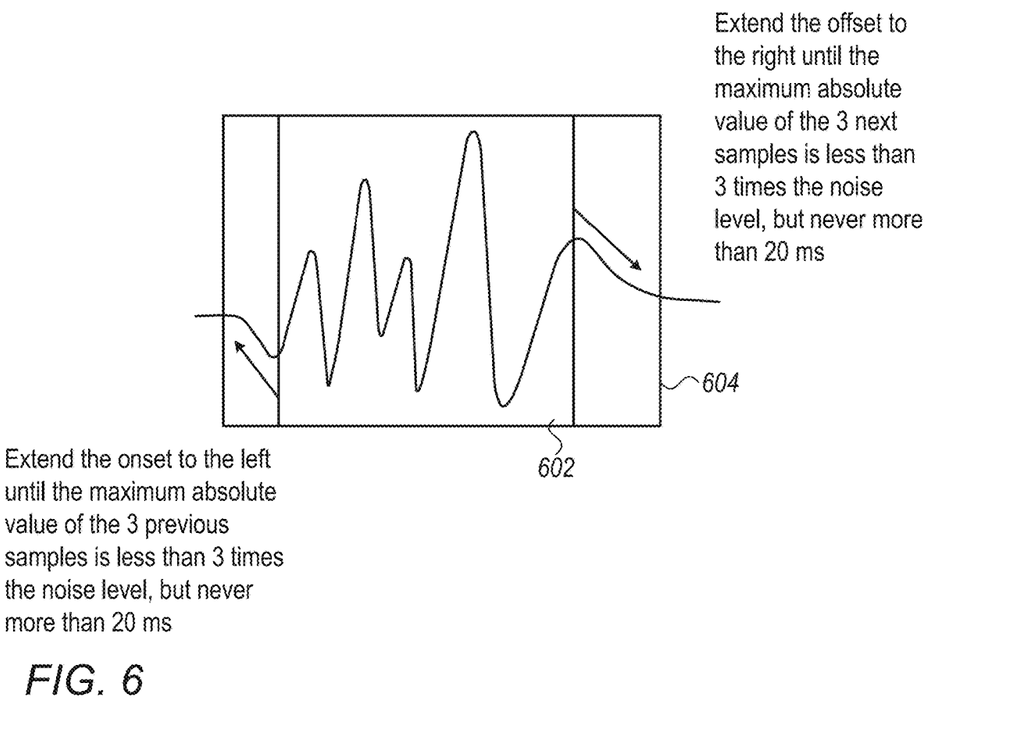
FIG. 6 is a graph that schematically illustrates the fine-tuning step of a fractionation duration described in FIG. 2, according to an example of the present disclosure.

Then, the onset and offset are extended by the processor by up to 20 ms on each side until each side is close enough to zero, which is assumed when the maximum of the absolute value of the next three samples falls below three times the baseline noise. This fine tuning step 218 is illustrated in FIG. 6.

The resulting time difference between the onset and offset of each candidate fractionation is also called hereinafter "duration" of the fractionation or "time frame" of the fractionation.

At a step 220, processor 28 stores the information regarding the onset and offset of the candidate fractionations, and the respective waveform. Once the time frame of the possible fractionation is calculated, processor 28 continues the algorithm by extracting features of the possible fractionation in steps 222-228, that are inputs of subsequent classification and scoring steps 230-232.

In some examples, once the candidate fractionations are identified and segmented in time, the processor extracts features of the fractionations used by a regression-based classifier to score the fractionations between benign ones and such that are very likely indicative of tissue locations causing a stable arrhythmia.

The logistic regression classifier that is used to calculate the fractionation score of the signal is given by:

$$\text{fractionation score} = \frac{10}{1 + e^{-(k_0 + F_1 \cdot k_1 + F_2 \cdot k_2 + F_3 \cdot k_3 + F_4 \cdot k_4 + F_5 \cdot k_5)}},$$

where $k_n$ are the coefficients of the logistic regression classifier. Since all features $F_n$ calculated below are positive real numbers, and $k_0$ is negative, the fractionation score may vary be between 0 and 10. A minimal score means a location unlikely to cause stable arrhythmia and a maximal score means a location very likely to cause stable arrhythmia.

The features fed into the regression classifier are:

F1←Duration of the time frame of the potential fractionation

F2←Number of fractionations in the time frame of the potential fractionation divided by the duration F3←Peak-to-peak voltage of the potential fractionation component divided by the duration F4←Natural log of 3+(number of wavefront candidates in the time frame of the potential fractionation in the current beat or in the most similar beat, whichever is larger)

F5←Number of zero crossings in the time frame of the potential fractionation divided by the duration F1 is already given in step 220.

In F4 extraction step 222, processor 28 counts the number of wavefront annotation candidates falling within the time frame of each potential (i.e., candidate) fractionation for the current beat, as well as for the most similar previous beat. The maximum number of annotation candidates among the current and the most similar previous beat is assumed to be the actual number of wavefront candidates.

Figure 7A:
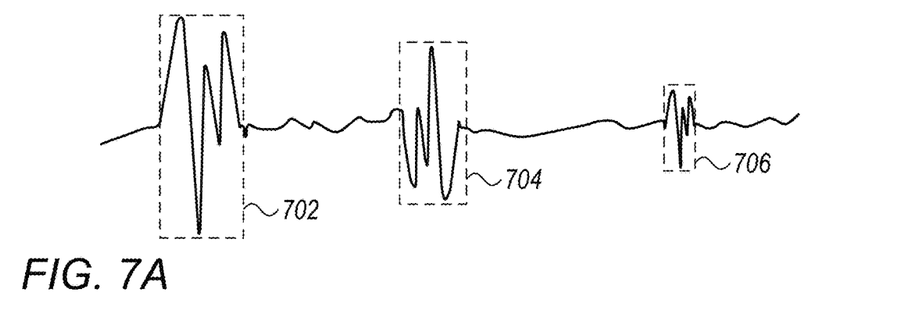
FIGS. 7A and 7B are illustrations of two types of signals, with the top line being schematic graphs of fractionations and the bottom line schematic graphs of noises, according to an example of the present disclosure.
Figure 7B:
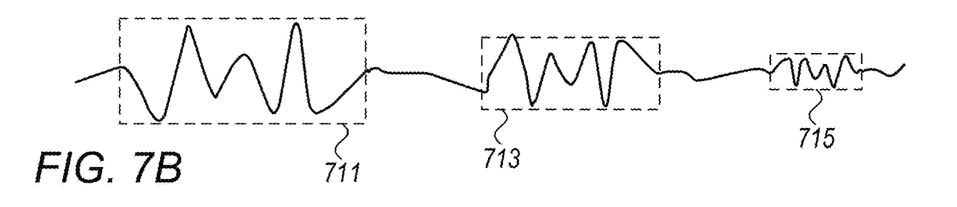

In F3 extraction step 224, processor 28 divides the peak amplitude of the fractionations by the relative duration. This feature contributes to the fractionation score negatively. A high aspect ratio, such as seen in FIG. 7 for signals in line (a) is indicative of either a normal signal or a noise. A low aspect ratio, such as seen in FIG. 7 in line (b) is indicative of a clinically meaningful fractionation. The rationale is, clinically meaningful fractionated signals appear, empirically, more frequently in low-voltage areas. Therefore, this feature, which has a negative coefficient in the logistic regression classifier, makes the system more sensitive to fractionations in low voltage areas, and more specific in high voltage areas.

At F2 extraction step 226, processor 28 calculates the number of fractionations (extrema of potential) within the time frame, taking into consideration only sharp fractionations (e.g., with an absolute slope larger than 3 μV between consecutive samples).

At F5 extraction step 228, processor 28 calculates the number of zero crossings within the time frame of the potential fractionation. This number is defined as the sum of upward and downward zero crossings.

An upward zero crossing is a zero or positive sample with a negative left neighbor A downward zero crossing is a zero or negative sample with a positive left neighbor Training The above logistic regression classifier model has five independent variables (features), thus six coefficients are required, including the intercept coefficient $k_0$.

Good classification results are considered such with an Event Per Variable (EPV) value of at least 20. The disclosed model has been trained with more than 1000 cases, therefore the EPV value in this training is more than 200. This value is an order of magnitude greater than the suggested value of 20. Therefore, the number of signals used in training can be considered as more than enough.

Each signal used in the training set has been tagged by three clinical account specialists and a SW engineer. Only unanimously tagged signals have been fed to the training. The rationale was not to confuse the classifier with ambiguous signals (given specificity is more important than sensitivity).

Inference (step 232)

Trained coefficients are stored as part of the algorithm. These coefficients are used to calculate the fractionation score. During the clinical study, the physician can select signals by their fractionation score and by other attributes. Some of the attributes are the duration of the potential fractionation and the peak-to-peak voltage. REF3 demonstrates that the duration of the activation and the voltage are good predictors of slow conduction areas. The physician is expected to use clinical judgement and experience to set the relevant thresholds for each one of the attributes, including for the fractionation score, in order to select signals that are relevant for the current clinical study.

Finally, at map generation step 234, processor 28 generates and displays an EP map to a user, such as the one shown in FIG. 8, overlaid with tissue locations scored according to their estimated impact on stable arrhythmia. Using a scoring scale on a GUI, the user can decide on a threshold score above which only tissue locations scored above that threshold are observed on the map.

The flow chart shown in FIG. 2 is chosen purely for the sake of conceptual clarity. The present example may also comprise additional steps of the algorithm, such as pre-selecting input EGMs based on indications of the degree of physical contact of the electrodes with diagnosed tissue from a contact force sensor. This and other possible steps are omitted from the disclosure herein purposely in order to provide a more simplified flow chart.

Figure 3:
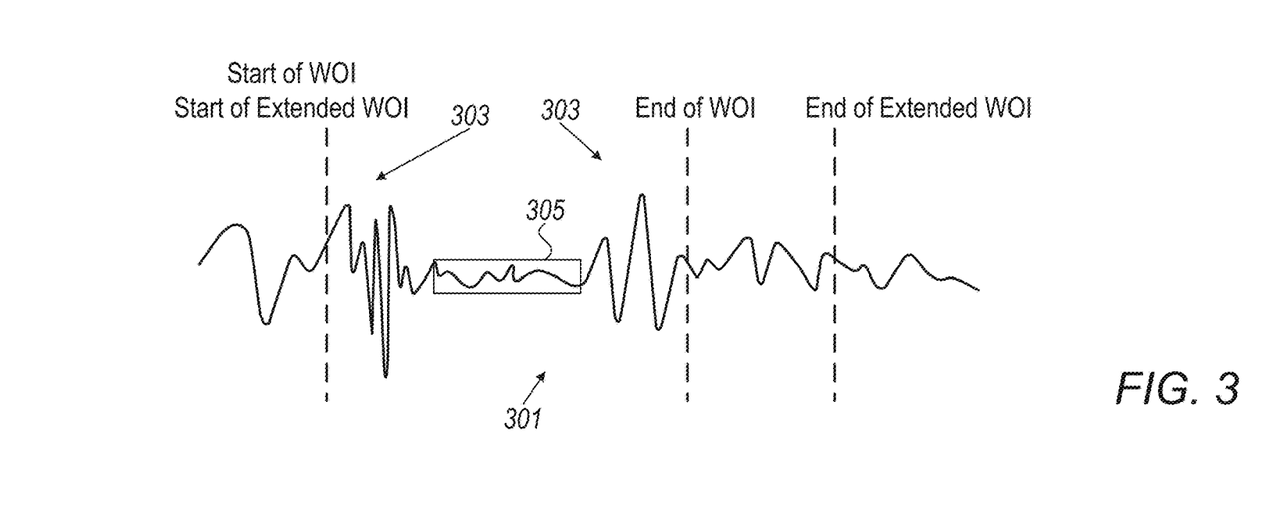
FIG. 3 shows an example graph of an electrogram acquired using the system of FIG. 1, the electrogram superimposed with an extended window of interest (WOI) in a step described in FIG. 2, according to an example of the present disclosure.

FIG. 3 shows an example graph of an electrogram 301 acquired using the system of FIG. 1, the electrogram 301 superimposed with a nominal and extended window of interest (WOI) in a step (203) described in FIG. 2, according to an example of the present disclosure. As seen, the disclosed extended WOI captures two candidate fractionations 303, since using the nominal WOI would have caused truncation and lose of the later (i.e., right) fractionation due to its falling in a clinically relevant mid-diastolic region of the cardiac cycle.

FIG. 3 further shows a "sliding maximum window" 305 with a width of a given segment (e.g., segment lasting 20%) of the cardiac cycle time used in calculating the baseline noise of the cardiac cycle in the aforementioned step 206.

FIG. 4 shows example graphs of an electrogram 402 acquired using the system of FIG. 1, and the signal 404 after applying the NLEO and Gaussian filter step described in FIG. 2 (the aforementioned step 210), according to an example of the present disclosure. As seen, the NLEO emphasizes the candidate fractionations, with the signal 404 slightly smoother than that of EGM 402.

FIG. 5 is a graph that schematically shows two fractionations with respective windows 501 found in step 212 described in FIG. 2, and an intersection region 505 of the windows, according to an example of the present disclosure. As seen, the two different windows have durations 511 and 513, with duration 513 of the current beat being longer than duration 511 of a previous beat. To consider durations in a subsequent set, an intersection region is defined between any two windows as the length of the shorter duration. Using the definitions, processor 28 fine tunes the onset of offset timings of the fractionations at the aforementioned fine tuning step 218. Thus, in the shown case, duration of intersection region 505 equals that of duration 511.

FIG. 5 further shows a duration 507 with no fractionation within it in an EGM 504. Processor 28 measures a "silence ratio" as time duration 507 with no fractionation within it, divided by total cycle time. This ratio serves to differentiate repeatable fractionations from irrelevant irregular ones.

FIG. 6 is a graph that schematically illustrates the fine tuning step of a fractionation duration described in FIG. 2 (in step 218), according to an example of the present disclosure. First, the onset and offset of the time frame is contracted up to the leftmost and rightmost extrema with a dV of at least baseline noise 3 µV or 5% of the peak-to-peak of the potential fractionation component, whichever is largest. This step yields time window 602.

Then, the onset and offset are extended by up to 20 ms on each side until each side is close enough to zero. This step yields time window 606. Close enough to zero is assumed when the maximum of the absolute value of the next three samples falls below three times the baseline noise.

FIGS. 7A and 7B are illustrations of two types of signals, with the top line (FIG. 7A) of schematic graphs (702, 704, 706) of fractionations, and the bottom line (FIG. 7B) of schematic graphs (711, 713, 715) of noises, according to an example of the present disclosure.

Signals 702-706 can be described as "probably fractionated." As seen, all three windows of signals 702-706 have a relatively high height/width aspect ratio. A physician probably would not erroneously call them "fractionations."

On the other hand, all three windows of signals 711-715 have relatively low height/width aspect ratios. The physician probably would erroneously consider these artifacts as real "fractionations."

Empirically, clinically meaningful fractionations are correlated with a lower peak-to-peak voltage. Thus, feeding the peak-to-peak voltage divided by the duration of the potential fractionation component automatically increases the fractionation score in low voltage areas, and vice-versa.

To overcome such biasing, the disclosed technique introduces the F3 enhancement feature in the above classification scoring function, in the form of peak-to-peak voltage of the potential fractionation component divided by the duration, i.e., to differentiate real fractionations from noise in scoring.

FIG. 8 is a schematic, pictorial volume rendering of an EP map of a ventricle indicating tissue locations and magnitude of fractionations that may cause a stable arrhythmia, according to an example of the present disclosure.

In the shown example, EP map 800 is a local activation time (LAT) map overlaid with fractionation score graphical indication 802 to indicate cardiac tissue locations exhibiting fractionations indicative of stable arrhythmia.

As noted above, a physician can adjust a scale 804 of the GUI to show only tissue location with a score above threshold (in the shown case, with a score>7).

Based on EP map 800, a physician, such as physician 27, can plan and perform a careful, selective ablation to eliminate a stable arrhythmia with minimal hazard to the patient.

Example 1

A method includes receiving a cardiac signal that is sensed by an electrode (22) at a tissue location inside the heart. Fractionations (303) are identified in the cardiac signal. The fractionations identified at the tissue location are compared between first and second cardiac cycles of the cardiac signal. Based on the comparing, a likelihood is estimated, that the tissue location is causing a stable arrhythmia. Based on the estimated likelihood, the tissue location is indicated to a user as likely to be causing the stable arrhythmia.

Example 2

The system according to example 1, wherein indicating the tissue location includes indicating to the user a score of the likelihood that the tissue location is causing the stable arrhythmia.

Example 3

The system according to example 1 or example 2, wherein indicating the tissue location includes recommending ablating the tissue location.

Example 4

The system according to example 1, wherein receiving the cardiac signal includes receiving a bipolar electrogram.

Example 5

The method according to example 1, wherein identifying the fractionations includes estimating baseline noise of the cardiac signal.

Example 6

The method according to example 5, wherein identifying the fractionations includes dynamically adjusting the threshold for a non-linear energy operator (NLEO) according to a ratio between a baseline noise and a peak-to-peak value of the EGM signal, the baseline noise given by a minimum value of a sliding maximum window of an absolute value of the signal.

Example 7

The method according to example 1, wherein identifying the fractionations includes comparing time periods of the cardiac signal in which at least a minimal predefined portion of the cardiac cycle does not contain any fractionation.

Example 8

The method according to example 1, wherein identifying the fractionations includes calculating, over a time interval, a ratio between peak-to-peak voltage of the cardiac signal and a duration of the time interval, and using the ratio to discriminate the fractionations from noise.

Example 9

The method according to example 1, wherein estimating the likelihood includes applying a logistic-regression-based classifier.

Example 10

The method according to example 1, wherein comparing the fractionations includes adjusting time-onset and time-offset of at least one of the fractionations.

Example 11

The method according to example 1, wherein identifying the fractionations in a given cardiac cycle includes using an extended window-of-interest (WOI) to capture all fractionations starting within a cardiac cycle.

Example 12

The method according to example 1, wherein estimating the likelihood is performed based on a number of zero crossings occurring in the cardiac signal within each fractionation.

Example 13

The method according to example 1, wherein estimating the likelihood is performed based on a number of local extrema occurring in a low-pass filtered cardiac signal within each fractionation.

Example 14

The method according to example 1, wherein comparing the fractionations includes representing fractionation windows as triangles.

Example 15

The method according to claim 1, wherein indicating the tissue location comprises generating and displaying an electrophysiological (EP) map (800) to the user, overlaid with a score of the likelihood that the tissue location is causing the stable arrhythmia.

Example 16

The method according to claim 16, and comprising, using a scale (804) on a graphical user interface (GUI), adjusting a threshold score above which only tissue locations whose score is above that threshold are displayed on the EP map (800).

Example 17

A system includes a memory (33), interface and a processor (28). The memory (33) is configured to store cardiac signals. The processor (28) is configured to (i) receive a cardiac signal that is sensed by an electrode (22) at a tissue location inside the heart (23), (ii) identify fractionations (303) in the cardiac signal, (iii) compare the fractionations, identified at the tissue location, between first and second cardiac cycles of the cardiac signal, (iv) based on the comparing, estimate a likelihood that the tissue location is causing a stable arrhythmia, and (v) based on the estimated likelihood, indicate the tissue location to a user as likely to be causing the stable arrhythmia.

Example 18

The system according to example 15, wherein the processor (28) is configured to indicate the tissue location by indicating to the user a score of the likelihood that the tissue location is causing the stable arrhythmia.

Example 19

The system according to example 15, wherein the processor (28) is configured to indicate the tissue location by generating and displaying an electrophysiological (EP) map (800) to the user, overlaid with a score of the likelihood that the tissue location is causing the stable arrhythmia.

Example 20

The system according to claim 16, and comprising a scale (804) on a graphical user interface (GUI), that the user can use to adjust a threshold score above which only tissue locations whose score is above that threshold are displayed on the EP map (800).

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and sub combinations of the various features described hereinabove, as well as variations and modifications thereof which would occur to persons skilled in the art upon reading the foregoing description and which are not disclosed in the prior art.

The invention claimed is:

1. A method, comprising:
receiving a cardiac signal that is sensed by an electrode at a tissue location inside the heart;
identifying fractionations in the cardiac signal;
comparing the fractionations, identified at the tissue location, between first and second cardiac cycles of the cardiac signal;
based on the comparing, estimating a likelihood that the tissue location is causing a stable arrhythmia; and
based on the estimated likelihood, indicating the tissue location to a user as likely to be causing the stable arrhythmia.

2. The method according to claim 1, wherein indicating the tissue location comprises indicating to the user a score of the likelihood that the tissue location is causing the stable arrhythmia.

3. The method according to claim 1, wherein indicating the tissue location comprises recommending ablating the tissue location.

4. The method according to claim 1, wherein receiving the cardiac signal comprises receiving a bipolar electrogram.

5. The method according to claim 1, wherein identifying the fractionations comprises estimating baseline noise of the cardiac signal.

6. The method according to claim 5, wherein identifying the fractionations comprises dynamically adjusting the threshold for a non-linear energy operator (NLEO) according to a ratio between a baseline noise and a peak-to-peak value of the EGM signal, the baseline noise given by a minimum value of a sliding maximum window of an absolute value of the signal.

7. The method according to claim 1, wherein identifying the fractionations comprises comparing time periods of the cardiac signal in which at least a minimal predefined portion of the cardiac cycle does not contain any fractionation.

8. The method according to claim 1, wherein identifying the fractionations comprises calculating, over a time interval, a ratio between peak-to-peak voltage of the cardiac signal and a duration of the time interval, and using the ratio to discriminate the fractionations from noise.

9. The method according to claim 1, wherein estimating the likelihood comprises applying a logistic-regression-based classifier.

10. The method according to claim 1, wherein comparing the fractionations comprises adjusting time-onset and time-offset of at least one of the fractionations.

11. The method according to claim 1, wherein identifying the fractionations in a given cardiac cycle comprises using an extended window-of-interest (WOI) to capture all fractionations starting within a cardiac cycle.

12. The method according to claim 1, wherein estimating the likelihood is performed based on a number of zero crossings occurring in the cardiac signal within each fractionation.

13. The method according to claim 1, wherein estimating the likelihood is performed based on a number of local extrema occurring in a low-pass filtered cardiac signal within each fractionation.

14. The method according to claim 1, wherein comparing the fractionations comprises representing fractionation windows as triangles.

15. The method according to claim 1, wherein indicating the tissue location comprises generating and displaying an electrophysiological (EP) map to the user, overlaid with a score of the likelihood that the tissue location is causing the stable arrhythmia.

16. The method according to claim 15, and comprising, using a scale on a graphical user interface (GUI), adjusting a threshold score above which only tissue locations whose score is above that threshold are displayed on the EP map.

17. A system, comprising:
a memory configured to store cardiac signals; and
a processor, which is configured to:
receive a cardiac signal that is sensed by an electrode at a tissue location inside the heart;
identify fractionations in the cardiac signal;
compare the fractionations, identified at the tissue location, between first and second cardiac cycles of the cardiac signal;
based on the comparing, estimate a likelihood that the tissue location is causing a stable arrhythmia; and
based on the estimated likelihood, indicate the tissue location to a user as likely to be causing the stable arrhythmia.

18. The system according to claim 17, wherein the processor is configured to indicate the tissue location by indicating to the user a score of the likelihood that the tissue location is causing the stable arrhythmia.

19. The system according to claim 17, wherein the processor is configured to indicate the tissue location by recommending ablating the tissue location.

20. The system according to claim 17, wherein the processor is configured to receive the cardiac signal by receiving a bipolar electrogram.

21. The system according to claim 17, wherein the processor is configured to identify the fractionations by estimating baseline noise of the cardiac signal.

22. The system according to claim 21, wherein the processor is configured to identify the fractionations by dynamically adjusting the threshold for a non-linear energy operator (NLEO) according to a ratio between a baseline noise and a peak-to-peak value of the EGM signal, the baseline noise given by a minimum value of a sliding maximum window of an absolute value of the signal.

23. The system according to claim 17, wherein the processor is configured to identify the fractionations by comparing time periods of the cardiac signal in which at least a minimal predefined portion of the cardiac cycle does not contain any fractionation.

24. The system according to claim 17, wherein the processor is configured to identify the fractionations by calculating, over a time interval, a ratio between peak-to-peak voltage of the cardiac signal and a duration of the time interval, and, using the ratio, to discriminate the fractionations from noise.

25. The system according to claim 17, wherein the processor is configured to estimate the likelihood by applying a logistic-regression-based classifier.

26. The system according to claim 17, wherein the processor is configured to compare the fractionations by adjusting time-onset and time-offset of at least one of the fractionations.

27. The system according to claim 17, wherein the processor is configured to identify the fractionations in a given cardiac cycle by using an extended window-of-interest (WOI) to capture all fractionations starting within a cardiac cycle.

28. The system according to claim 17, wherein the processor is configured to estimate the likelihood based on a number of zero crossings occurring in the cardiac signal within each fractionation.

29. The system according to claim 17, wherein the processor is configured to estimate the likelihood based on a number of local extrema occurring in a low-pass filtered cardiac signal within each fractionation.

30. The system according to claim 17, wherein the processor is configured to compare the fractionations by representing fractionation windows as triangles.

31. The system according to claim 17, wherein the processor is configured to indicate the tissue location by generating and displaying an electrophysiological (EP) map to the user, overlaid with a score of the likelihood that the tissue location is causing the stable arrhythmia.

32. The system according to claim 31, and comprising a scale on a graphical user interface (GUI), that the user can use to adjust a threshold score above which only tissue locations whose score is above that threshold are observed on the EP map.

* * * * *